(12) United States Patent
Hovis et al.

(10) Patent No.: US 6,245,956 B1
(45) Date of Patent: Jun. 12, 2001

(54) METHOD FOR SEPARATING SULFONE FROM A HYDROCARBON STREAM HAVING A SMALL CONCENTRATION OF SULFONE

(75) Inventors: Keith W. Hovis; Harold R. Hunt; Robert B. Eldridge, all of Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 08/388,532

(22) Filed: Feb. 14, 1995

(51) Int. Cl.[7] .................................................. C07C 7/10
(52) U.S. Cl. ............................ 585/868; 585/833
(58) Field of Search ........................... 585/833, 868

(56) References Cited

U.S. PATENT DOCUMENTS

| | | | |
|---|---|---|---|
| 3,488,920 | 1/1970 | Hutchinson | 55/56 |
| 5,191,150 | 3/1993 | Child et al. | 585/809 |
| 5,237,122 | * 8/1993 | Eastmen et al. | 585/709 |
| 5,262,579 | 11/1993 | Child et al. | 585/802 |
| 5,264,647 | 11/1993 | Eastman et al. | 585/724 |
| 5,264,649 | * 11/1993 | Eastman et al. | 585/802 |
| 5,347,065 | * 9/1994 | Anderson et al. | 585/724 |

* cited by examiner

*Primary Examiner*—Walter D. Griffin
*Assistant Examiner*—Nadine Preisch
(74) *Attorney, Agent, or Firm*—Charles W. Stewart

(57) ABSTRACT

Described is a process for separating sulfone from a hydrocarbon having a small concentration of said sulfone by use of water as an extraction solvent.

9 Claims, 2 Drawing Sheets

METHOD FOR SEPARATING SULFONE FROM A HYDROCARBON STREAM HAVING A SMALL CONCENTRATION OF SULFONE

The present invention relates to a process for separating sulfone from a hydrocarbon stream which contains a small concentration of such sulfone.

It has recently been discovered that sulfone additives can be utilized in combination with traditional hydrogen fluoride alkylation catalysts as a means for reducing the volatility of the resultant catalyst mixture. One side effect from utilizing a sulfone additive in combination with a hydrofluoric acid alkylation catalyst is that small concentrations of sulfone become dissolved in the resultant alkylate product. The small concentration of sulfone in the alkylate product can have a negative impact on the alkylate as a gasoline blend component. Thus, even though the concentration of sulfone is very small, it is desirable to remove such small concentrations of sulfone from an alkylate product in order to prevent its negative economic consequences on refiners who use the alkylate as a gasoline blending component.

It is thus an object of this invention to provide a method for removing sulfone that is contained in an alkylate reaction product.

It is further an object of this invention to provide a process for separating a small concentration of sulfone contained in an alkylation reaction product which contains a concentration of such sulfone.

Thus, the process of the present invention includes separating sulfone from a hydrocarbon stream which contains a concentration of a sulfone. This process includes extracting the sulfone from the hydrocarbon stream by contacting such hydrocarbon stream with water. The water serves as an extraction solvent and thus extracts at least a portion of the sulfone contained in the hydrocarbon stream and provides an extract stream which is enriched with the sulfone and comprises water. A raffinate stream is produced which has a concentration of sulfone that is smaller than the concentration of sulfone in the original hydrocarbon stream which is contacted with the extraction solvent.

An additional embodiment of the invention relates to a method for removing sulfone from a hydrocarbon stream having a sulfone concentration of less than about 1 weight percent. The hydrocarbon stream is contacted with a water solvent and an extract stream enriched with sulfone and comprising water is recovered. Also recovered is a raffinate stream comprising a hydrocarbon having a concentration of sulfone that is below that of the sulfone concentration of the hydrocarbon stream.

Figure 1:
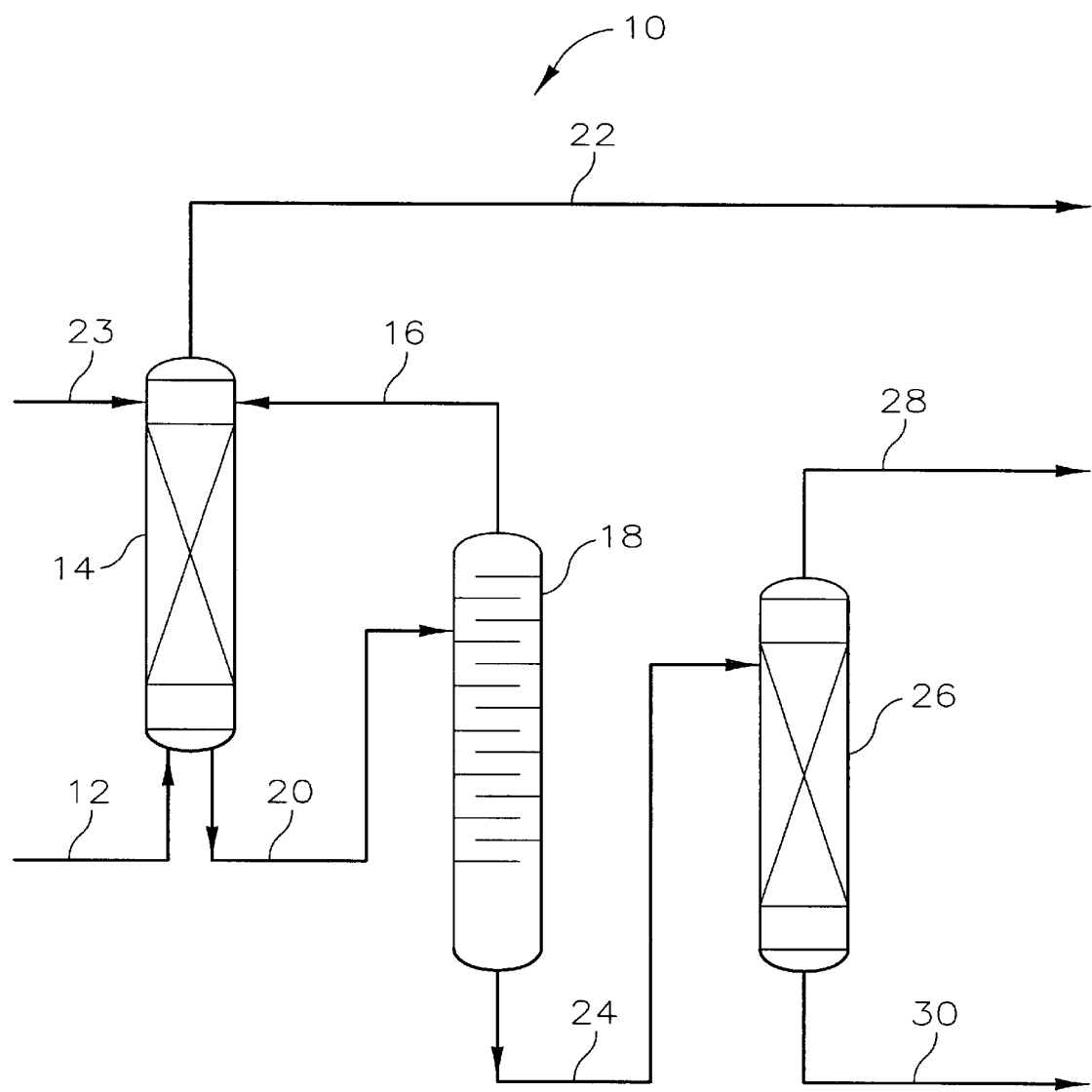
Figure 2:
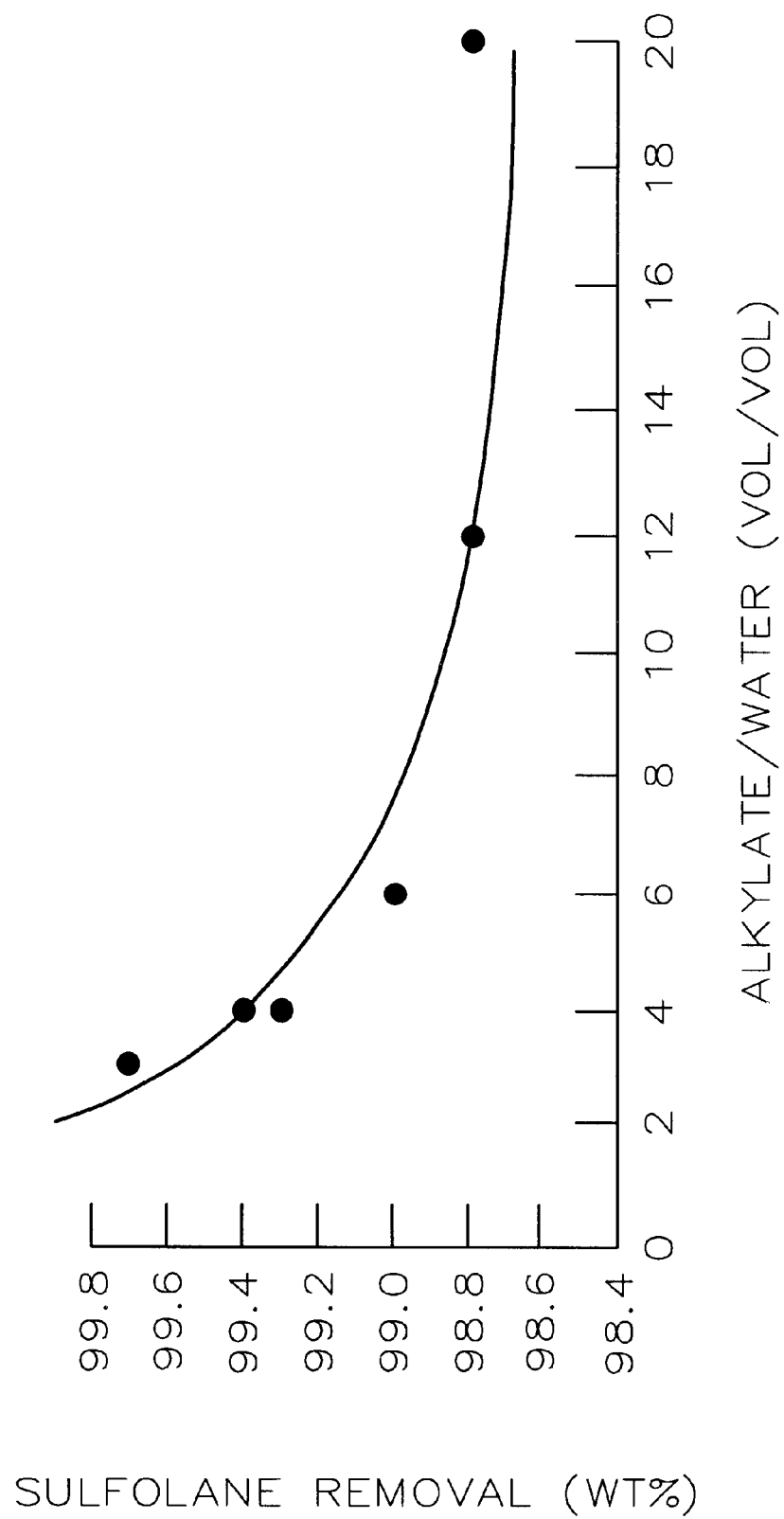

In the accompanying drawings:

FIG. 1 provides a schematic representation of the process which is one embodiment of the invention; and FIG. 2 is a plot of extraction data for water as an extractant for removing sulfolane from alkylate.

The process of this invention contemplates the resolution of problems associated with a gasoline blending component containing a small concentration of a sulfone compound. This sulfone compound, in sufficient concentrations, serves as a contaminant to a gasoline end-product when it is contained in a gasoline blending component such as an alkylate product produced by the catalytic alkylation of olefins and isoparaffins. In particular, recently it has been discovered that a novel catalyst which utilizes a sulfone as one component in combination with hydrogen fluoride can provide for a suitable alkylate product. One problem encountered, however, is that when utilizing a mixture of the hydrogen fluoride and sulfone as an alkylation catalyst, due to the slight solubility of sulfone in hydrocarbon, there is a small concentration of the sulfone that passes from the alkylation reaction system along with the alkylate end-product. It is, thus, critical that a significant portion of the sulfone contained in the alkylate end-product be removed prior to utilizing it as a gasoline blending component. The need to remove the sulfone concentration is important even though the sulfone is only slightly soluble in the alkylate hydrocarbon and that the concentration levels typically will not exceed 2 or 3 weight percent of the alkylate product.

It is, therefore, important to remove a significant portion of the sulfone concentration in a hydrocarbon stream which contains such sulfone. Generally, it is necessary that at least a portion of the sulfone is removed from the hydrocarbon stream, which can be at least about 70 weight percent of the sulfone concentration. Preferably, it is desirable to remove at least about 80 weight percent of the sulfone contained in the hydrocarbon stream and, most preferably, it is desirable to remove at least 90 weight percent of the sulfone concentration in the hydrocarbon stream. In fact, the novel process described herein has the exceptional ability under proper process conditions of removing at least 99 weight percent of the sulfone contained in the hydrocarbon stream when the sulfone concentration is less than about 1 weight percent.

The hydrocarbon stream of the invention generally will include hydrocarbons having from 3 to 12 carbon atoms and with the most common hydrocarbons being paraffins. Specifically, the hydrocarbon stream will be an alkylate hydrocarbon product comprising paraffins produced by the catalytic reaction of olefins and isoparaffins of an alkylation process. The alkylation catalyst utilized in the alkylation process comprises a sulfone component and hydrogen fluoride. The alkylation catalyst utilized in the alkylation of the olefins and isoparaffins generally will have a weight ratio of hydrogen fluoride to sulfone in the range of about 1:1 to about 40:1. A preferred weight ratio of hydrogen fluoride to sulfone in the alkylation catalyst can range from about 2.3:1 to about 19:1 and, more preferably, it can range from 3:1 to 9:1.

Alkylation processes contemplated in the present invention are those liquid phase processes wherein mono-olefin hydrocarbons such as propylene, butylenes, pentylenes, hexylenes, heptylenes, octylenes and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant, and the olefin reactant is selected from propylene, butylenes, pentylenes and mixtures thereof for production of an alkylate hydrocarbon product comprising a major portion of highly branched, high octane value aliphatic hydrocarbons having at least seven carbon atoms and less than ten carbon atoms.

The sulfones suitable for use in this invention are the sulfones of the general formula

wherein R and R' are monovalent hydrocarbon alkyl or aryl substituents, each containing from 1 to 8 carbon atoms. Examples of such substituents include dimethylsulfone, di-n-propylsulfone, diphenylsulfone, ethylmethylsulfone and the alicyclic sulfones wherein the $SO_2$ group is bonded to a hydrocarbon ring. In such a case, R and R' are forming together a branched or unbranched hydrocarbon divalent moiety preferably containing from 3 to 12 carbon atoms. Among the latter, tetramethylenesulfone (tetrahydrothiopene-1,1-dioxide) or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures.

Because of a slight solubility of sulfone in the alkylate hydrocarbon product, there will be a small concentration of sulfone therein. Generally, the sulfone concentration is less than about 1 weight percent of the total weight of the alkylate hydrocarbon product and, specifically, it can range from about 0.01 weight percent to about 1.0 weight percent depending on processing conditions. Ordinarily, the sulfone concentration in the alkylate hydrocarbon product can range from about 0.1 weight percent to about 0.9 weight percent and, most likely, it can range from 0.15 weight percent to 0.5 weight percent.

Because of the contamination caused by an excessive concentration of sulfone in the alkylate hydrocarbon product, it is desirable to remove at least a portion of the sulfone in the alkylate hydrocarbon product so as to have a gasoline blending component that can suitably be blended with other gasoline components to produce a desirable gasoline end-product. Thus, a substantial portion of the sulfone content of the alkylate hydrocarbon product is removed by the inventive process of this invention which can be at least about 70 weight percent of the sulfone contained in the alkylate hydrocarbon product. Preferably, it is desirable to remove at least about 80 weight percent of the sulfone content of the alkylate hydrocarbon product and, most preferably, it is desirable to remove at least 90 weight percent of the sulfone content. Because of the efficiency of the process of this invention, it is even possible under appropriate process conditions to remove upwardly to 99 weight percent, or more, of the sulfone contained in the hydrocarbon alkylation product.

The alkylate hydrocarbon product is contacted with an extraction solvent comprising, consisting of, or consisting essentially of, water. Any suitable contacting means for contacting the extraction solvent with the alkylate hydrocarbon product can be used for providing intimate mixing or contacting the extraction solvent with the alkylate hydrocarbon product. Such contacting means as plate columns, packed columns or single stage contacting means, which include static mixers and mechanically agitated vessels, may be used. Thus, any means which provides for the intimate contacting or mixing of the extraction solvent with the alkylate hydrocarbon product may be used as a part of this invention.

Any amount of extraction solvent relative to the quantity of the alkylate hydrocarbon product can be utilized in the process provided the amount of extraction solvent contacted with the alkylate hydrocarbon product is effective for the removal of at least a portion of the sulfone contained in the alkylate hydrocarbon product. Generally, contacting efficiency requires an amount of extraction solvent with the alkylate hydrocarbon product such that the volumetric ratio of water contacted with the alkylate hydrocarbon is at least about 0.01:1 water to hydrocarbon. Preferably, the volumetric ratio of water contacted with hydrocarbon is at least about 0.05:1 and, most preferably, the volumetric weight ratio can exceed 0.1: 1. Economics will generally set the upper limit for the volumetric ratio of water to alkylate hydrocarbon product.

An extract stream enriched with sulfone and comprising water is recovered from the contacting means. The extract stream will contain at least a portion of the sulfone contained in the alkylate hydrocarbon product and can contain, as earlier described herein, at least about 70 weight percent of the sulfone contained in such alkylate hydrocarbon product. Also recovered from contacting means is a raffinate stream which comprises the alkylate hydrocarbon product and has a reduced sulfone concentration below that of the alkylate hydrocarbon product.

Referring now to FIG. 1, there is presented a schematic representation of process 10 which depicts a liquid-liquid extraction process system utilized for the extraction of a sulfone solute from an alkylate hydrocarbon product. The alkylate hydrocarbon product stream, which comprises an alkylate product having a concentration of sulfone, passes by way of conduit 12 to extractor 14. Extractor 14 defines a contacting zone and provides contacting means for contacting the alkylate hydrocarbon product with an extraction solvent comprising water. The extraction solvent is introduced into extractor 14 via conduit 16 which is operably connected in fluid flow communication between fractionator 18 and extractor 14. An extract is recovered from extractor 14 by way of conduit 20 which is operatively connected in fluid flow communication between extractor 14 and fractionator 18. The recovered extract comprises water with at least a portion of the sulfone contained in the alkylate hydrocarbon product and passes to fractionator 18. Fractionator 18 defines a fractionation zone and provides for the separation of water and sulfone.

A raffinate stream which is the alkylate hydrocarbon product stream having a substantially reduced concentration of sulfone contained therein passes from extractor 14 by way of conduit 22. The recovered water from fractionator 18 may, if desired, be returned to extractor 14 by way of conduit 16. Makeup water is conveyed to extractor 14 through conduit 23. The sulfone recovered from the extraction solvent passes by way of conduit 24 from fractionator 18 to vacuum tower 26. Conduit 24 is operatively connected and provides for fluid flow communication between fractionator 18 and vacuum tower 26. Vacuum tower 26 defines a fractionation zone and provides means for separating the sulfone from the water contained in the sulfone stream exiting fractionator 18. The overhead from vacuum tower 26 passes by way of conduit 28 and comprises primarily water recovered from the fractionator 18 bottoms stream. The purified sulfone component will pass from vacuum tower 26 by way of conduit 30. The recovered sulfone component, which passes from vacuum tower 26 by way of conduit 30, can be recycled or reused as a sulfone component of the alkylation reaction process. The water recovered by way of conduit 28 can be either disposed of or reused as an extraction solvent.

The following examples are provided to further illustrate the present invention. The examples are provided by way of illustration only. They are not intended as a limitation upon the invention as set out in the appended claims.

EXAMPLE 1

The following calculated example is to illustrate the benefits achievable from the novel process as illustrated in FIG. 1. Table I shows the mass flows corresponding to the numbered streams of FIG. 1. As can be seen from the material balance of Table I, the alkylate hydrocarbon product passing through conduit 12 contains more than 0.1 weight percent sulfolane, and the raffinate stream contains less than 0.001 weight percent sulfolane. Over 99 weight percent of the sulfolane contained in the alkylate hydrocarbon product is removed therefrom by the novel process.

TABLE I

Material Balance for Process of FIG. 1

| Mass Flows | Stream | | | | | | | |
|---|---|---|---|---|---|---|---|---|
| | 12 | 16 | 20 | 22 | 23 | 24 | 28 | 30 |
| Pentanes | 118828.2 | 0.3 | 0.3 | 118828.2 | 0.0 | 0.0 | 0.0 | 0.0 |
| Hexanes | 118828.2 | 0.0 | 0.0 | 118828.2 | 0.0 | 0.0 | 0.0 | 0.0 |
| Heptanes | 962097.5 | 0.9 | 0.9 | 962097.5 | 0.0 | 0.0 | 0.0 | 0.0 |
| Octanes | 1950013.0 | 0.1 | 0.1 | 1950013.0 | 0.0 | 0.0 | 0.0 | 0.0 |
| Nonanes | 124974.5 | 0.0 | 0.0 | 124974.5 | 0.0 | 0.0 | 0.0 | 0.0 |
| C10+ | 821143.8 | 0.0 | 0.0 | 821143.8 | 0.0 | 0.0 | 0.0 | 0.0 |
| Water | 0.0 | 377520.2 | 381335.5 | 3837.4 | 7652.7 | 3815.3 | 3800.7 | 14.6 |
| Sulfolane | 4889.2 | 4.0 | 4856.5 | 36.7 | 0.0 | 4852.5 | 0.5 | 4852.0 |
| Total | 4100774.2 | 377525.5 | 386193.3 | 4099759.2 | 7652.7 | 8667.8 | 3801.2 | 4866.6 |

EXAMPLE II

Example II presents data obtained from extraction experiments using water as an extraction solvent for removing sulfolane from alkylate. An alkylate feed containing, on average, 1082 wppm sulfolane was charged to a commercially available one inch, stirred, York-Scheibel extractor containing approximately 8 theoretical stages. The data obtained are present in Table II and are charted in FIG. 2. As the data show, water can be an effective solvent for extracting sulfolane contained in a hydrocarbon solution. The water solvent is effective in removing more than 99 weight percent of the sulfolane contained in an alkylate. The weight percent sulfolane removed increases with increasing water to alkylate ratios.

TABLE II

| Water/Alkylate Ratio (vol/vol) | Sulfolane Removal (weight percent) | Alkylate/Water Ratio (vol/vol) |
|---|---|---|
| 0.050 | 98.8 | 20 |
| 0.083 | 98.8 | 12 |
| 0.167 | 99.0 | 6 |
| 0.250 | 99.3 | 4 |
| 0.250 | 99.4 | 4 |
| 0.330 | 99.7 | 3 |

While this invention has been described in terms of the presently preferred embodiment, reasonable variations and modifications are possible by those skilled in the art. Such variations and modifications are within the scope of the described invention and the appended claims.

That which is claimed:

1. A process for separating sulfone from a paraffin hydrocarbon alkylation product, including hydrocarbons having from 3 to 12 carbon atoms, containing a concentration of a sulfone, said process comprises:
   extracting said sulfone from said paraffin hydrocarbon alkylation product by contacting said paraffin hydrocarbon alkylation product with water thereby to extract at least a portion of said sulfone from said paraffin hydrocarbon alkylation product and to provide an extract stream enriched with said sulfone and comprising water and a raffinate stream having a reduced concentration of said sulfone below said concentration of said sulfone in said paraffin hydrocarbon alkylation product.

2. A process as recited in claim 1 wherein said concentration of said sulfone in said paraffin hydrocarbon alkylation product is less than about 1 weight percent.

3. A process as recited in claim 2 wherein said at least a portion of said sulfone represents at least about 70 weight percent of said sulfone in said paraffin hydrocarbon alkylation product.

4. A process as recited in claim 3 wherein said sulfone is sulfolane.

5. A process as recited in claim 4 wherein the weight ratio of water contacted with said paraffin hydrocarbon alkylation product is at least at about 0.01:1 water to hydrocarbon.

6. A method for removing sulfone from a paraffin hydrocarbon alkylation product, including hydrocarbons having from 3 to 12 carbon atoms, having a sulfone concentration, said method comprising:
   contacting said paraffin hydrocarbon alkylation product, having said sulfone concentration which is less than about 1 weight percent, with a solvent comprising water;
   recovering an extract stream enriched with sulfone; and
   recovering a raffinate stream comprising said paraffin hydrocarbons, having from 3 to 12 carbon atoms, and having a reduced sulfone concentration below said sulfone concentration.

7. A method as recited in claim 6 wherein said extract stream contains at least 70 weight percent of said sulfone of said paraffin hydrocarbon alkylation product.

8. A method as recited in claim 7 wherein said sulfone is sulfolane.

9. A method as recited in claim 8 wherein the weight ratio of said solvent contacted with said paraffin hydrocarbon alkylation product is at least about 0.01:1 solvent to hydrocarbon.

* * * * *